(12) United States Patent
Xu et al.

(10) Patent No.: US 9,266,933 B2
(45) Date of Patent: Feb. 23, 2016

(54) POLYPEPTIDES INHIBITING NEOVASCULARIZATION AND USES THEREOF

(71) Applicant: SHANGHAI FIRST PEOPLE'S HOSPITAL, Shanghai (CN)

(72) Inventors: Xun Xu, Shanghai (CN); Ying Zheng, Shanghai (CN)

(73) Assignee: SHANGHAI FIRST PEOPLE'S HOSPITAL, Shanghai (CN)

( * ) Notice: Subject to any disclaimer, the term of this patent is extended or adjusted under 35 U.S.C. 154(b) by 0 days.

(21) Appl. No.: 14/370,114

(22) PCT Filed: Oct. 29, 2012

(86) PCT No.: PCT/CN2012/083671
§ 371 (c)(1),
(2) Date: Jul. 1, 2014

(87) PCT Pub. No.: WO2013/060303
PCT Pub. Date: May 2, 2013

(65) Prior Publication Data
US 2015/0111827 A1    Apr. 23, 2015

(30) Foreign Application Priority Data
Oct. 28, 2011    (CN) .......................... 2011 1 0335251

(51) Int. Cl.
| | | |
|---|---|---|
| A61K 38/00 | (2006.01) | |
| A61P 35/00 | (2006.01) | |
| C07K 14/515 | (2006.01) | |
| C07K 14/47 | (2006.01) | |
| A61K 38/18 | (2006.01) | |
| A61K 9/00 | (2006.01) | |

(52) U.S. Cl.
CPC ........... *C07K 14/4703* (2013.01); *A61K 9/0048* (2013.01); *A61K 38/1891* (2013.01); *C07K 14/515* (2013.01)

(58) Field of Classification Search
None
See application file for complete search history.

(56) References Cited

U.S. PATENT DOCUMENTS

| | | | | |
|---|---|---|---|---|
| 5,919,899 A | * | 7/1999 | Persico et al. | 530/350 |
| 2009/0068679 A1 | * | 3/2009 | Vitzthum et al. | 435/7.1 |

FOREIGN PATENT DOCUMENTS

| | | | | |
|---|---|---|---|---|
| CN | 1653177 | | 8/2005 | |
| WO | WO9206194 | * | 4/1992 | C12N 15/16 |
| WO | 2006/001888 | | 1/2006 | |
| WO | 2006/128553 | | 12/2006 | |
| WO | 2013/060020 | | 5/2013 | |

OTHER PUBLICATIONS

Gassmann et al. Efficient production of chicken egg yolk antibodies against a conserved mammalian protein. The FASEB Journal, 1990. vol. 4, pp. 2528-2532.*
International Search Report for international application No. PCT/CN2012/083671, dated Feb. 7, 2013 (10 pages).
International Preliminary Report on Patentability for international application No. PCT/CN2012/083671, dated Apr. 29, 2014 (10 pages).
D. Diana et al., "β-Hairpin Peptide Targeting VEGF Receptors: Design, NMR Characterization and Biological Activity," JBC Papers in Press. Published Oct. 3, 2011 as Manuscript M11.257402, found online at http://www.jbc.org/cgi/doi/10.1074/jbc.M111.257402 (24 pages).
A. Eriksson et al., "Placenta Growth Factor-1 antagonizes VEGF-induced angiogenesis and tumor growth by the formation of functionally inactive PIGF-1/VEGF heterodimers," Cancer Cell, vol. 1, Feb. 2002, p. 99-108.
D. Ribotti, Abstract of "The discovery of the placental growth factor and its role in angiogenesis: a historical review," Angiogenesis, (2008) vol. 11, No. 3, p. 215-21 (1 page).
Y. Cao, "Positive and Negative Modulation of Angiogenesis by VEGFRI Ligands," Science Signaling, Feb. 2009, vol. 2, No. 59, p. 1-11.
D. Diana et al., "β-Hairpin Peptide That Targets Vascular Endothelial Growth Factor (VEGH) Receptors, Journal of Biological Chemistry: Design, NMR Characterization, and Biological Activity," vol. 286, No. 48, (2011) p. 41680-41691.

* cited by examiner

*Primary Examiner* — Marcela M Cordero Garcia
(74) *Attorney, Agent, or Firm* — Hamre, Schumann, Mueller & Larson, P.C.

(57) ABSTRACT

Provided is a polypeptide having angiogenesis inhibiting activity. The polypeptide is derived from Placenta Growth Factor-1. Also provided are a derivative polypeptide of the polypeptide, a preparation method for polypeptide, and a pharmaceutical composition containing the polypeptide.

10 Claims, 4 Drawing Sheets

POLYPEPTIDES INHIBITING NEOVASCULARIZATION AND USES THEREOF

TECHNICAL FIELD

The present invention relates to biomedicine. In particular, the present invention relates to a novel small peptide inhibiting angiogenesis, and said small peptide is a polypeptide derived from Placenta Growth Factor (PLGF). The present invention also relates to a method for preparing the polypeptide, uses thereof, and a pharmaceutical composition comprising the polypeptide.

TECHNICAL BACKGROUND

Angiogenesis involves extremely complicated courses including expansion of existing vessels, increase in vascular permeability, degradation of perivescular stroma, activation, proliferation and migration of endothelial cells, and formation of new capillary-like lumina.

About ⅔ of diseases causing blindness are associated with pathological angiogenesis in eyes, for example, corneal angiogenesis induced by simplex herpetic stromal keratitis, choroidal angiogenesis in age-related macular degeneration, and retinal angiogenesis in diabetic retinopathy or retinopathy of premature infant. At present, laser photocoagulation, photodynamic therapy (PDT), and thermal transpupillary therapy (TTT) etc. are conventionally used for clinically treating the ocular pathological angiogenesis. However, these treatments tend to destroy local tissues, and the long-term efficacy thereof is still unsatisfactory. Therefore, in recent years, people kept trying to develop more effective methods for treating ocular pathological angiogenesis.

When developing effective inhibitors of angiogenesis, the specificity of the ocular drugs should be sufficiently considered.

Firstly, there are many anatomical and functional barriers in eyes. Systemic administration usually cannot result in a topically sufficient drug concentration in ocular tissue due to the blood-aqueous humor barrier and blood-retina barrier. Theoretically, in topical administration, such as injection in vitreous cavity, it is difficult for any macromolecule larger than 76.5 kDa to penetrate the retina and act on the retinal and choroidal angiogenesis. When administrated on ocular surface, the drugs have to successively penetrate lipophilic the corneal epithelial cells as well as the hydrophilic corneal stroma, which are the tightly connected. Thus, merely the medications that have appropriate lipophilicity, a low molecular weight or capability to bind with the transporters (e.g., amino acid transporters, oligopeptide transporters, etc.) in ocular surface tissues can reach the anterior chamber and function effectively.

Secondly, the solubility of the drugs in the hydrophilic tears, aqueous humor, and vitreous humor is positively correlated to their effects.

Thirdly, for the above major reasons, the bioavailability of ocular drugs is very low. To improve it, the administration concentration of drugs should be increased. However, compounds for treating neoplastic angiogenesis exhibit significant toxicity, so that high dose cannot be used in either systemic or topical administration. In addition, exogenous proteins with large molecular weight are also sensitive foreign substances which may cause immune damages to eye tissues such as uveal.

Fourthly, currently a series of relatively safe endogenous inhibitors of angiogenesis, such as angiostatin consisting of plasminogen Kringle domains 1-4, have been demonstrated to significantly inhibit growth of vessel blood-dependent tumor. However, due to their relative large molecular weight and complicated spatial conformation, these inhibitors have disadvantages in preparation such as complicated recombinant expression and purification processes, residual endotoxin and so on. Because of the constraints caused by the above factors, at present, only a few medicaments are used for treating ocular angiogenesis, e.g., recombinant anti-VEGF monoclonal antibody bevacizumab (Avastin), and the recombinant fragment of anti-human VEGF monoclonal antibodies ranibizumab (Lucentis), etc. However, they are expensive, repeated intravitreal administrations are necessary, and certain risks, such as vascular embolization will be caused.

Thus, for preventing and treating neovascular eye diseases, it is extremely important to seek for the small-molecule inhibitors with specific biological activity and biocompatibility, which can penetrate all kinds of barriers in ocular tissue via non-invasive or minimally invasive administration, thereby enhancing ocular bioavailability with reduced dosage, reduced side effects either locally or systemically. Therefore, there is an urgent need in developing small molecule inhibitors of angiogenesis, which are safe, effective, and compatible with eyeball tissues.

SUMMARY OF INVENTION

The purpose of the present invention is to provide a small molecular polypeptide, and the fragments, analogs, and derivatives thereof, which are suitable for eyeball tissue, effective and safe for inhibit angiogenesis.

Another purpose of the present invention is to provide a method for preparing said polypeptide and use of said polypeptide.

In the first aspect, the present invention provides a polypeptide represented by the following formula I, or a pharmaceutically acceptable salt thereof, wherein,
Xaa0 is absent, or a peptide segment consisting of 1-3 amino acids;
Xaa1 is selected from the group consisting of Thr and Ser;
Xaa2 is selected from the group consisting of Ala, Val, Leu and Ile;
Xaa3 is selected from the group consisting of Asn, Gln, His, Lys and Arg;
Xaa4 is selected from the group consisting of Val, Ile, Leu, Met, Phe and Ala;
Xaa5 is selected from the group consisting of Thr and Ser;
Xaa6 is selected from the group consisting of Met, Leu, Phe, or Ile;
Xaa7 is selected from the group consisting of Gln and Asn;
Xaa8 is selected from the group consisting of Leu, Ile, Val, Met, Ala and Phe;
Xaa9 is selected from the group consisting of Leu, Ile, Val, Met, Ala and Phe;

Xaa10 is selected from the group consisting of Lys, Arg, Gln and Asn;

Xaa11 is selected from the group consisting of Ile, Leu, Val, Met, Ala and Phe;

Xaa12 is selected from the group consisting of Arg, Pro, Lys, Gln and Asn;

Xaa13 is selected from the group consisting of Ser and Thr;

Xaa14 is selected from the group consisting of Gly, Pro, and Ala;

Xaa15 is selected from the group consisting of Asp, Glu;

Xaa16 is selected from the group consisting of Arg, Lys, Gln and Asn;

Xaa17 is selected from the group consisting of Pro and Ala;

Xaa18 is selected from the group consisting of Ser and Thr;

Xaa19 is selected from the group consisting of Tyr, Trp, Phe, Thr and Ser;

Xaa20 is selected from the group consisting of Val, Ile, Leu, Met, Phe and Ala;

Xaa21 is selected from the group consisting of Glu and Arg;

Xaa22 is selected from the group consisting of Leu and Ser;

Xaa23 is selected from the group consisting of Thr and Arg;

Xaa24 is selected from the group consisting of Phe and Ser;

Xaa25 is selected from the group consisting of Ser and Arg;

Xaa26 is selected from the group consisting of Gln and Ser;

Xaa27 is selected from the group consisting of His and Arg;

Xaa28 is absent, or a peptide segment consisting of 1-3 amino acids;

and said polypeptide exhibits an activity of inhibiting angiogenesis and has a length of 27-33 amino acids.

In another preferred embodiment, said polypeptide has a length of 28-31 amino acids.

In another preferred embodiment, Xaa28 is a peptide segment consisting of 3 amino acids.

In another preferred embodiment, Xaa0 is absent, or a peptide segment consisting of 1, 2 or 3 amino acid(s).

In another preferred embodiment, Xaa0 is selected from Lys, Glu, Pro-Ile-Lys, or Ile-Lys.

In another preferred embodiment, said polypeptide is selected from the group consisting of:

(a) a polypeptide having the amino acid sequence represented by SEQ ID NO:1;

(b) a polypeptide which is derived from the polypeptide of (a) by substitution, deletion, or addition of 1-5 amino acids (preferably 1-3, and more preferably 1-2) in the amino acid sequence of SEQ ID NO: 1 and which has the activity of inhibiting angiogenesis.

In another preferred embodiment, said derived polypeptide retains ≥70% activity to inhibit angiogenesis of polypeptide represented by SEQ ID NO.: 1.

In another preferred embodiment, the identity between said derived polypeptide and SEQ ID No.: 1 is ≥80%, preferably ≥90%; and more preferably ≥95%.

The present invention further provides a dimer form and a polymer form of the compound of formula I, which exhibit the activity of inhibiting angiogenesis.

In the second aspect, the present invention provides an isolated nucleic acid molecule encoding the above polypeptide of the present invention.

In the third aspect, the present invention provides a pharmaceutical composition comprising:

(a) the above polypeptide or a pharmaceutically acceptable salt thereof of the present invention; and (b) a pharmaceutically acceptable carrier or excipient.

In another preferred embodiment, the composition is in the form of eyedrop, injection solution (such as injection solution for periocular or intraocular injection), ophthalmic gel or eye ointment.

In another preferred embodiment, the composition is in a sustained release dosage form.

In the fourth aspect, the present invention provides a use of said polypeptide or a pharmaceutically acceptable salt thereof for preparing a medicament for inhibiting angiogenesis, or preventing or treating diseases associated with angiogenesis.

In another preferred embodiment, the disease associated with angiogenesis is selected from the group consisting of neovascular eye diseases, tumor, ischemic heart disease, non-inflammatory myocardiopathy, coronary sclerosis, arteriosclerosis obliterans, artery embolism, artery thrombus, Berger's disease, chronic inflammation, inflammatory intestinal diseases, ulcer, rheumatic arthritis, scleroderma, psoriasis, infertility or sarcoma-like diseases.

In another preferred embodiment, the neovascular eye diseases include diseases involved in choroid, retina, cornea or iris, including age-related macular degeneration, proliferative diabetic retinopathy, retinal vessel-blocked diseases, retinopathy of prematurity, corneal infection, and neovascular glaucoma.

In the fifth aspect, the present invention provides a method for inhibiting angiogenesis in mammal, comprising the step of administering the polypeptide or a pharmaceutically acceptable salt thereof of the present invention to a subject in need thereof.

In another preferred embodiment, the subject is a human.

In another preferred embodiment, the angiogenesis is associated with neovascular eye diseases.

It should be understood that in the present invention, the technical features specifically described above and below (such as the Examples) can be combined with each other, thereby constituting a new or preferred technical solution which needs not be described one by one.

DESCRIPTION OF DRAWINGS

The following descriptions of drawings are intended to illustrate the specific embodiments of the present invention, but not to limit the scope of the present invention, which should be defined by the claims.

FIG. 3a, FIG. 3b, and FIG. 3c show that ZY3 inhibits the lumen formation of HUVECs. FIG. 3a is the VEGF group; FIG. 3b is the VEGF+ZY3(160 μM) group; FIG. 3c indicates that in groups of VEGF with Small peptide ZY3 in different concentrations, lumen formation of HUVECs is significantly inhibited. *$P<0.05$. The differences are statistically significant.

FIGS. 4a-4c show the count results of 3-5 subordinate microvessels in the area within 2.5 mm around the filter paper. FIG. 4a is the PBS group; FIG. 4b is the ZY3(10 μl 1/piece) group; FIG. 4c is the ZY3(50 μl/piece) group; FIG. 4d shows that, compared with the VEGF group, in the groups of VEGF+ small peptide ZY3 with different concentrations, the neovascularization of chick embryo chorioallantoic membrane is significantly inhibited and the inhibition is concentration-dependent. **P<0.01. The differences are statistically significant.

FIGS. 5a-5c show the neovascularization area on mouse cornea. FIG. 5a is the VEGF group; FIG. 5b is the ZY3(0.5 μl/granule) group; FIG. 5c is the ZY3(2 μl 1/granule) group; FIG. 5d shows that, compared with the VEGF group, in the groups of VEGF+ small peptide ZY3 with different concentrations, the pathological angiogenesis in mouse cornea is significantly inhibited. **P<0.01. The differences are statistically significant.

DETAILED DESCRIPTION OF THE INVENTION

After extensive and intensive studies, the inventors have firstly prepared a class of small molecular polypeptides derived from Placental Growth Factor, exhibiting a function of angiogenesis inhibition and having a molecular weight of less than 5 kD (for example, just about 3 KD). In particular, by utilizing the method of bioinformatics, the inventor designed several candidate sequences based on the homology analysis and analysis on the biological properties. After synthesizing these sequences via solid phase synthesis, obtaining small peptide ZY3 with high purity upon purification and further screening through the model of vessels on chick embryo chorioallantoic membrane, the model of VEGF induced HUVECs proliferation and lumen formation, the mouse model of VEGF induced corneal angiogenesis, and the mouse model of corneal micro-capsule, the inventors obtained a class of novel, small molecular polypeptides exhibiting the function of preventing and treating angiogenesis.

The molecular weight of small peptides of the present invention is small, enabling the peptides penetrating through various ocular tissue barriers. They have good water solubility, so that they can maintain a relatively high concentration in neutral tears, aqueous humor and vitreous humor. They are highly safe with a minor toxicity or side-effect to the biological tissue. The bioavailability is high through local application in the eye, thereby reducing either the dose or the systemic toxicity. Based on the above works, the present invention is completed.

Placenta Growth Factor

Placenta Growth Factor (PlGF) is one of the VEGF family. PlGF was separated and purified by Maglione et. al from the DNA library of human placenta as early as 1991. PlGF could be detected in heart, lung, thyroid, skeletal muscles besides in human placenta. Based on the selective splicing of PlGF genes, 4 different isoforms in molecular size, secretion features, and receptor affinity could be formed: PlGF-1 (PlGF131), PlGF-2(PlGF152), PlGF-3(PlGF203), and PlGF-4(PlGF224). Two PlGF monomers form secreted homodimer glycoprotein, and then bind to their receptors, thereby mediating the following signal transduction and exerting their biological effects. In addition, heterodimers could be formed by combining PlGF with VEGF to affect the signal transduction pathway of VEGF. PlGF can promote proliferation of endothelial cells, especially microvascular endothelial cells and it can be used as the chemokine for endothelial cells growth factor to regulate endothelial cells growth and stimulate angiogenesis. PlGF can further promote the migration of monocytes and endothelial cells to increase the permeability of endothelial cells. Although angiogenesis can also be induced by VEGF, the new blood vessel induced by PlGF exhibits normal physiological characteristics without any other abnormality. The new blood vessel induced by PlGF won't exhibit phenomena, such as edema, hemangioma and increased permeability due to the VEGF induced angiogenesis.

Active Polypeptides

In the present invention, the terms "the polypeptide(s) of the present invention", "polypeptide(s) ZY3", "small peptide(s) ZY3", "short peptide(s) ZY3" and "peptide(s) ZY" are interchangeably used and refer to a protein or polypeptide having peptide ZY3 amino acid sequence (TANVTM-QLLKIRSGDRPSYVELTFSQH, SEQ ID NO: 1) and exhibiting an activity of inhibiting angiogenesis. In addition, said terms comprise the variants of SEQ ID NO: 1 which exhibit the function of inhibiting angiogenesis. These variations include, but are not limited to, deletions, insertions and/or substitutions of 1-5 (typically 1-4, preferably 1-3, more preferably 1-2, most preferably 1) amino acids, and addition of one or more (typically less than 5, preferably less than 3, more preferably less than 2) amino acids at C-terminus and/or N-terminus. For example, a protein's functions are usually unchanged when an amino residue is substituted by a similar or analogous one in the art. Further, the addition of one or several amino acids at C-terminus and/or N-terminus generally will not change the structure and function of protein. Furthermore, the terms also include the polypeptide of the present invention in monomer and polymer form. The terms also include the linear and nonlinear polypeptides (such as cyclic peptides).

The present invention further includes the active fragments, derivatives and analogs of ZY3 polypeptide. As used herein, the terms "fragments", "derivatives" and "analogs" refer to the polypeptides substantially maintaining the function or activity of inhibiting angiogenesis. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of ZY3 polypeptide with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6H is. According to the subject application, these fragments, derivatives and analogs are within the scope commonly known by the skilled person.

A class of preferred active derivatives is the polypeptides formed by replacing at most 5, preferably at most 3, more preferably at most 2, most preferably 1 amino acid of the amino acid sequence represented by formula I with the amino acid having similar or analogous property. These conservative variant polypeptides are preferably formed by carrying out the amino acid replacement according to Table I.

TABLE I

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the analogues of ZY3 polypeptide. These analogues differ from naturally occurring ZY3 polypeptide in amino acid sequence or modifications that do not affect the sequence, or by both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acelylation, or carboxylation. Glycosylation is also included in modification, e.g., the polypeptides produced by glycosylation modification during its synthesis and processing or in the further processing steps. These modifications can be achieved by exposing the polypeptide to enzymes for glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals (such as sodium, potassium, calcium or magnesium), and esters, carbamate or other conventional "prodrug" forms.

Encoding Sequences

The present invention further relates to a polynucleotide encoding ZY3 polypeptide. A preferred encoding sequence which encodes ZY3 short peptide as shown in SEQ ID NO.: 1 is (SEQ ID NO: 2:
ACGGCCAATGTCACCATGCAGCTCCTAAAGATCCGTTCTGGGGACCGGC

CCTCCTACGTGGAGCTGACGTTCTCTCAGCAC).

The polynucleotide of the present invention can be in a form of DNA or RNA. DNA can be the coding strand or the non-coding strand. The coding sequence encoding the mature polypeptide can be identical to the coding sequence indicated in SEQ ID NO: 2, or can be a degenerate variant thereof. As used herein and taking SEQ ID NO.: 2 as an example, "degenerate variant" refers to a nucleic acid sequence which encodes the protein having the amino acid sequence of SEQ ID NO:1, but is different from the corresponding coding sequence in SEQ ID NO: 2.

ZY3 full-length nucleotide sequence or a fragment thereof of the present invention can be obtained via PCR amplification, recombination method or artificial synthesis. Currently, the DNA sequence encoding the polypeptide (or a fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell engineered by the vector or the coding sequence of the ZY polypeptide of the present invention.

In another aspect, the present invention further comprises polyclonal antibodies or monoclonal antibodies specific to ZY3 polypeptide, especially the monoclonal antibodies.

Preparation Method

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

One preferred method is to use liquid phase synthesis technique or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylformamide for 20 minutes under room temperature to remove the Fmoc protective groups. Then the sequence is extended from the C-terminus to the N-terminus one-by-one according to the predetermined amino acid sequence. After synthesis, trifluoroacetic acid containing 4% p-methylphenol is used to cleave the preinsulin-relevant peptide from the resin and the protective groups are removed. The resin can be filtered, and the crude peptide can be obtained via precipitation with ether. The solution of the resulting product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine (DIEA)/dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular screen Sephadex G10 or Tsk-40f. Then the desired peptide is obtained via high pressure liquid purification. Various coupling agents and coupling methods known in the peptide chemistry can be used to couple each amino acid residue. For example, dicyclohexyl-carbodiimide (DCC), hydroxylbenzotriazole (HOBt) or 1,1,3,3-tetramethyluronium Hexafluorophosphate (HBTU) can be used for direct coupling. The purity and structure of the resulting short peptide can be verified by reverse phase HPLC and mass spectrometry.

In a preferred embodiment, the polypeptide ZY3 of the present invention is prepared by solid phase method according to its sequence, purified by high performance liquid chromatography, thereby obtaining freeze-dried powder of target peptide with high purity. The powder is stored at −20° C.

Another method is to produce the polypeptide of the present invention by a recombination technique. With the conventional recombinant DNA technique, the polynucleotide of the present invention can be used to express or produce recombinant ZY3 polypeptides. Generally, the method comprises the following steps:

(1) Transforming or transfecting a suitable host cell with a polynucleotide or variant thereof encoding the ZY3 polypeptide of the present invention or a recombinant expression vector containing said polynucleotide;

(2) Culturing the host cell in a suitable culture medium;

(3) Isolating and purifying protein from the culture medium or cell.

The recombinant polypeptide may be expressed in cells or on the cell membrane, or secreted out of the cell. If desired, the physical, chemical and other properties can be utilized in various isolation methods to isolate and purify the recombinant protein. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

It is also contemplated to link multiple polypeptides of the present invention in series due to the short length of the peptide. After recombinant expression, the expression product is obtained in a form of polymer. Then the polymer is enzymatically cleaved to form the desired small peptides.

Pharmaceutical Composition and Methods of Administration

In another aspect, the present invention further provides a pharmaceutical composition, comprising (a) a safe and effective amount of the polypeptide of the present invention or a pharmaceutically acceptable salt thereof, and (b) a pharmaceutically acceptable carrier or excipient. The amount of the polypeptide of the present invention generally is 10 µg to 100 mg per dose, preferably 100-1000 µg per dose.

For the purpose of the invention, the effective dose is about 0.01 mg to 50 mg of the polypeptide of the present invention per kg body weight, preferably 0.05 mg to 10 mg of the polypeptide of the present invention per kg body weight administered to an individual. Further, the polypeptide of the present invention can be used alone, or in combination with the other therapeutic agents (for example, formulated into the same pharmaceutical composition).

The pharmaceutical composition can further comprise a pharmaceutically acceptable carrier. The term "pharmaceutically acceptable carrier" refers to the carrier for using in administering the therapeutic agents. The term refers to such medical carriers that they themselves do not induce antibody deleterious to the subject having been administered the composition, and they do not have excessive toxicity after administration. These carriers are well known by the skilled person in the art. The detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or the combination thereof.

The pharmaceutically acceptable carrier in the therapeutic composition can comprise liquid, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulated the composition of the present invention can be administered via conventional routes which include, but are not limited to, administering on ocular surface, around the eye, intraocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include eyedrop, injection, ophthalmic gel, and eye ointment.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulation can be carried out in a conventional manner according to the dosage form.

For example, formulation of eyedrop can be prepared as follows: dissolving short peptide ZY or a pharmaceutically acceptable salt thereof and the basic substances in sterile water (surfactant is dissolved in said water), adjusting osmotic pressure and pH to the physiological level, optionally adding suitable medical additives, such as preservatives, stabilizing agents, buffering agents, isotonicities, anti-oxidants and tackifiers, and then completely dissolving them.

The pharmaceutical composition of the present invention can further be administered in a form of sustained release formulation. For example, the short peptide ZY or salt thereof can be incorporated into the pill or microcapsule in which a sustained release polymer is used as carrier, and then the pill or microcapsule is implanted into the tissue to be treated by operation. Furthermore, the short peptide ZY3 or salt thereof can be used by insertion of intraocular lens pre-coated with said drugs. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples of the sustained release polymer include the biodegradable polymers, such as polymer of lactic acid, and lactic acid-glycolic acid copolymer.

When the pharmaceutical composition of the present invention is used in the actual treatment, the dose of the short peptide ZY3 or a pharmaceutically acceptable salt thereof, as an active ingredient, can be suitably determined according to the body weight, age, sex, symptom of each patient. For example, when topically dropping in the eye, the concentration of the active ingredient generally is 0.1-10 wt %, preferably 1-5 wt %, and the composition can be administrated for 2-6 times per day with 1-2 drops each time.

INDUSTRIAL APPLICABILITY

The pharmaceutical composition containing the peptide of the present invention or a pharmaceutically acceptable salt thereof as an active ingredient exhibits significant inhibition activity on angiogenesis. As verified by animal tests, the polypeptide of the present invention not only can inhibit angiogenesis in chick embryo chorioallantoic membrane, but also can inhibit the proliferation, migration, chemotaxis and lumen formation of HUVEC and the retinal angiogenesis in the hypoxia-induced mice.

The main advantages of the present invention include:

(a) The polypeptide ZY3 of the present invention has small molecular weight, so that it can penetrate ocular tissue barrier.

(b) The polypeptide of the present invention has good water solubility, so that it can maintain relatively high concentration in neutral tears, aqueous humor and vitreous humor.

(c) The polypeptide of the present invention has high safety with less toxicity to the tissue of the organism. The bioavailability in eye topical administration is high, thus the dose can be reduced, and the systemic toxicity can also be reduced.

(d) The polypeptide of the present invention can be synthesized via solid phase synthesis with high purity, high yield and low cost.

(e) The polypeptide of the present invention is highly stable.

Therefore, the polypeptide of the present invention can be developed into a medicine for treating neovascular eye diseases and related diseases associated with angiogenesis, such as tumor angiogenesis, etc.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Synthesis, Separation and Purification of Small Peptide ZY3

The polypeptides ZY3 represented by SEQ ID NO: 1 were synthesized by using the commercially available SYMPHONY polypeptide synthesizer (12-channel, Protein Technologies. LLC., U.S.). The processes were as follows:

The reagents were calculated and prepared according to the software (Version. 201) of the polypeptide synthesizer. 2-Chlorotrityl Chloride Resin (Nankai Synthetic Technology Co., Ltd, Tianjin, China) was added into a reaction tubes, DMF (15 ml/g) (Dikma) was added and the tube was oscillated for 30 min. Solvents were suction filtered out through the sintered filter. 3-fold excess mole of Fmoc-L-OH (small peptide ZY3) amino acids (Suzhou Tianma Pharma Group Specialty Chemicals Co., Ltd.) was added and then 10-fold excess mole of DIEA (Sinopharm Shanghai Chemical Reagent Company) was added and finally, DMF was added for dissolution. The mixture was oscillated for 30 min. DMF was removed and 20% piperidine (Sinopharm Shanghai Chemical Reagent Company) solution in DMF (15 ml/g) was added to react for 5 min. DMF was removed and another 20% piperidine solution in DMF (15 ml/g) was added to react for 15 min. Piperidine solution was suction filtered. A dozen granules of resin were taken out and washed for three times with ethanol. A droplet of ninhydrin solution, a droplet of KCN solution, and a droplet of phenol solution were added respectively. Then, the mixture was heated at 105° C.-110° C. for 5 min and the change of color into dark blue indicated the positive reaction. The resins were washed with DMF (10 ml/g, twice), methanol (10 ml/g, twice), and DMF (10 ml/g, twice). 3-fold excess of both protected amino acids (FOMC-Asp-OH) and HBTU (Suzhou Tianma Pharma Group Specialty Chemicals Co., Ltd.) were added respectively. They were dissolved with little DMF and added into the reaction tube. Then 10-fold excess of NMM was immediately added and mixture was reacted for 30 min. It was washed with DMF (10 ml/g) once, methanol (10 ml/g) twice, and DMF (10 ml/g) twice. The above steps were repeated and the amino acids were connected from right to left according to the sequence of small peptides ZY3. After the connection of the last amino acid, the deprotection was carried out and the resins were washed with DMF (10 ml/g, twice), methanol (10 ml/g, twice), DMF (10 ml/g, twice) and DCM (10 ml/g, twice) respectively. Then the resins were drained for 10 min. The polypeptides were cleaved from the resins (cleavage fluid (10/g): 94.5% TFA (J. T. Baker), 2.5% water, 2.5% EDT (ALDRICH), 1% TIS (ALDRICH); cleavage time: 120 min). Residual liquid containing protein was sufficiently dried with nitrogen (Shanghai Biou Gas Industry Ltd.), washed for six times with diethyl ether (Shanghai Shiyi Chemical Reagents Ltd.), and then dried at room temperature.

Polypeptides were purified with HPLC (Models of SHIMADZU HPLC device: preparation model/analytical model. Software: Class-VP, Sevial System, manufacturer: Shimadzu). The crude peptides were dissolved with pure water or small amount of acetonitrile (Fisher) and small peptides ZY3 were purified under the following conditions:

Pump A: 0.1% trifluoroacetic acid+ultrapure water

Pump B: 0.1% trifluoroacetic acid+acetonitrile

Flow rate: 1.0 ml/min

Detection volume: 30 μl

Wavelength: 220 nm

Detection column: Column:Venusi MRC-ODS C18 (30× 250 mm)

The detection processes are shown in table 2

TABLE 2

| Time (min) | A (%) | B (%) |
|---|---|---|
| 0.5 | 90 | 10 |
| 30.0 | 20 | 80 |
| 30.1 | stop | |

Finally, the purified solution was lyophilized to obtain small peptides ZY3 with high purity (>95%).

Example 2

Identification and Storage of Small Peptides ZY3

A small amount of small peptides ZY3 was taken for purity identification by HPLC analysis and molecular weight identification by ESI-MS.

Figure 1:
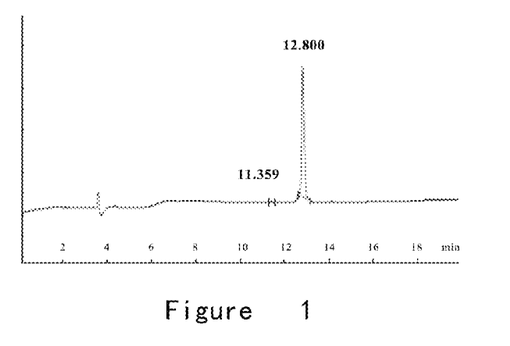
FIG. 1 shows the purity identification of the Small peptide ZY3 analyzed by High Performance Liquid Chromatography (HPLC).

The results showed that the elution peak of ZY3 was at 12.8 min with the purity over 99% (FIG. 1).

Small peptide ZY3 has 27 amino acids in total with a molecular weight of 3092.55.

The small peptides in white powder form were sealed, packaged, and stored at −20° C.

Example 3

Effect of Small Peptides ZY3 on Proliferation Activity of HUVECs

The MTS method was used as follows:
Primary Human Umbilical Vein Endothelial Cells (HUVECs) (purchased from ScienCell Co.) were inoculated into a 96-well plate with an inoculation concentration of $2×10^4$/ml. After cells had adhered to the wall, serum-free culture medium ECM was added and the cells were cultivated at 37° C. for 24 hours. Then the serum-free culture medium ECM as negative control, VEGF (100 ng/ml) (purchased from Sigma Co.) as positive control, VEGF (100 ng/well)+small peptide ZY3 in different concentrations as treatment groups were added in each well. After a 24-hour incubation, 20 μl 1 MTS solution (purchased from Promega Corporation) was added in each well. After incubation at 37° C. for 4 hours, the absorbance in each well was measured at 490 nm by using microplate reader (Bio-Rad Co.). The proliferation activity of cells was determined according to OD490. Finally, SPSS11.0.1 was used for statistical analysis.

Figure 2:
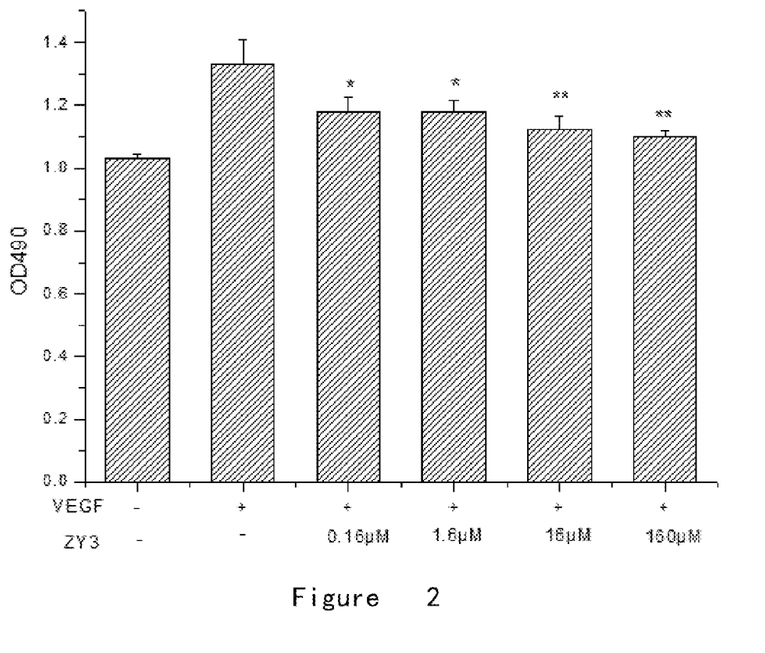
FIG. 2 shows the effect of Small peptide ZY3 on proliferation of Human Umbilical Vein Endothelial Cells (HUVECs). Small peptide ZY3 has a significant effect of inhibiting the proliferation of endothelial cells. Compared with VEGF group, in groups of VEGF+ZY3 peptide, the proliferation of HUVECs are significantly inhibited. *$P<0.05$, **$P<0.01$. The differences are statistically significant.

The results shown in FIG. 2 indicated that small peptide ZY3 significantly inhibited the proliferation of HUVECs and the inhabitation was concentration-dependent. Compared with VEGF group, in groups of VEGF+ peptide ZY3 the proliferation of HUVECs was significantly inhibited. *P<0.05, **P<0.01. The differences are statistically significant.

Example 4

Effect of Small Peptide ZY3 on Lumen Formation of HUVECs

The Matrigel method was used as follows:
A 50 μl/well Matrigel (purchased from BD Co.) was added into a 96-well plate, and then the plate was incubated at 37° C. for 30 min. Upon solidification, the primary HUVECs were inoculated onto the surface of Matrigel with an inoculation concentration of $8×10^6$/ml. Then the serum-free culture medium ECM as negative control, VEGF (100 ng/ml) (purchased from Sigma Co.) as positive control, VEGF (100 ng/well)+small peptide ZY3 in different concentrations as treatment groups were added in each well. The plate wad incubated at 37° C. After treating for 6 hours, photos were taken for cells in 3 randomized fields in the plate under the microscope (×200 fold.), and the sum of the maximum lumina diameter formed in the cells was calculated. Finally, SPSS11.0.1 was used for statistical analysis.

Figure 3:
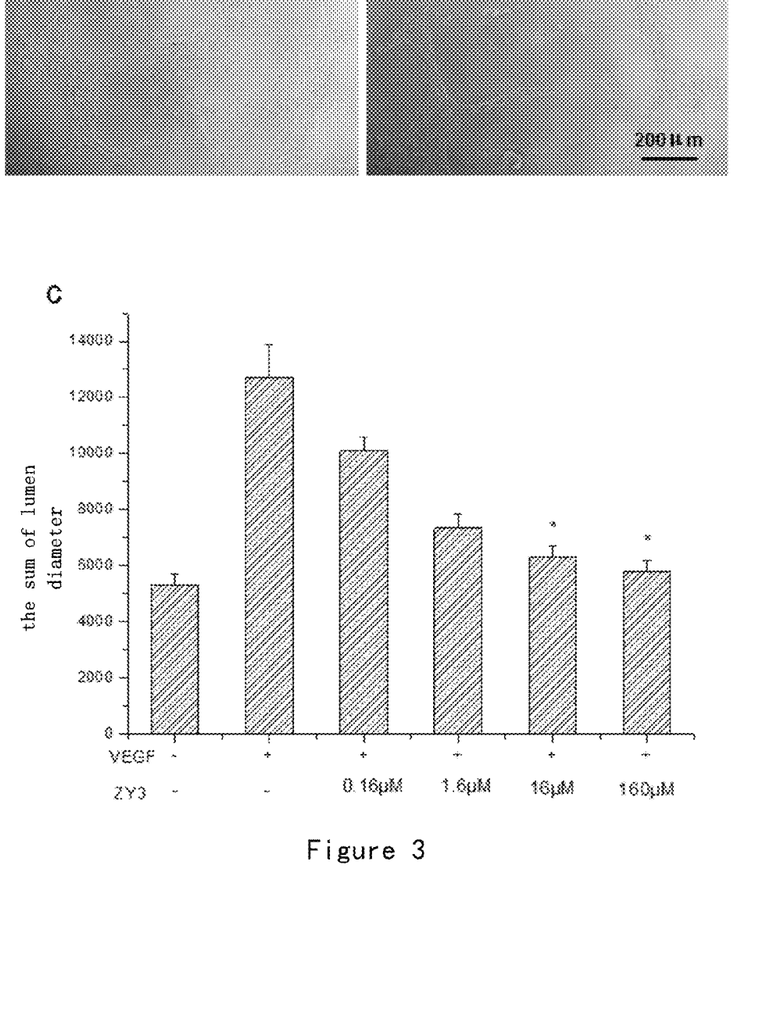
FIG. 3 shows the effect of Small peptide ZY3 on lumen formation of Human Umbilical Vein Endothelial Cells (HUVECs). Small peptide ZY3 exhibits a significant effect of inhibiting the lumen formation of endothelial cells.

The results shown in FIG. 3 indicated that small peptide ZY3 started to inhibit the lumen formation of HUVECs at the $6^{th}$ hour and the effect was concentration-dependent. FIG. 3a-3c showed the lumen formation inhibition effects of small peptide ZY3 on HUVECs. FIG. 3a is the VEGF group; FIG. 3b is the VEGF+ZY3 (160 μM) group; FIG. 3c indicates that in groups of VEGF with Small peptide ZY3 in different concentration, lumen formation of HUVECs is significantly inhibited, compared with the VEGF group.*P<0.05. The differences are statistically significant.

Example 5

Detection of Inhibition Effect of Small Peptides ZY3 on Angiogenesis in Chick Embryo Chorioallantoic Membrane Model of chick embryo chorioallantoic membrane was used and the methods were as follows:
Upon sterilization, the chick fertile eggs of 1-2 days old (purchased from 36 Lianhuaqing Chicken Farm of Shanghai Xinghuo Farm) were placed into a thermhygrostat (purchased from Shanghai Boxun industrial Co., ltd. SPX-250C) (T=37° C., Humidity H=60-70%) to incubate for 5 days. Every day, the eggs were overturned for one time at morning and night. Onto the filter paper (Whatman quantitative filter papers, Sigma, ashless, Grade 42, Cat No 1442-042, 42.5 mm Φ×100 circles) containing cortisone acetate (5 μg/μl, 5 μl/piece), PBS (5 μl/piece), low (2 μg/μl) or high (10 μg/μl) concentration of small peptides ZY3 (5 μl/piece) were dropped respectively. After air-dried, the filter paper was placed between the major vessels on chorioallantoic membrane of fertile eggs and the eggs were sealed. The eggs were placed in the thermhygrostat (T=37° C., Humidity H=60-70%) to incubate for another 2 days (24 hours a day) without overturning. Then the chorioallantoic membrane was thoroughly exposed and photographed (the range was within 5 mm around the filter paper). The number of 3-5 subordinate microvessels in the area within 2.5 mm around the filter paper was counted. SPSS11.0.1 was used for statistical analysis.

Figure 4:
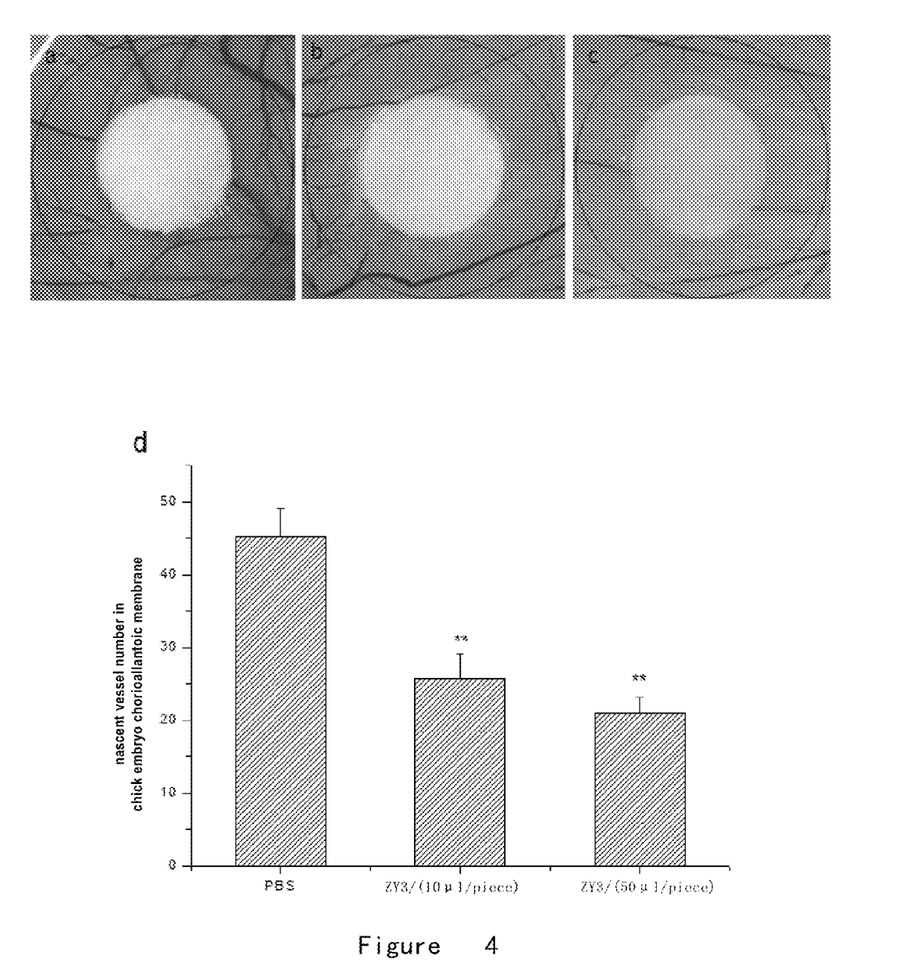
FIG. 4 shows the effect of Small peptide ZY3 on angiogenesis in chick embryo chorioallantoic membrane: Small peptide ZY3 exhibits a significant effect on anti-angiogenesis.

The results shown in FIG. 4 indicated that compared with PBS group, small peptide ZY3 exhibits significant inhabitation effects on angiogenesis of chick embryo chorioallantoic membrane both in low (10 μg/piece) and high (50 μg/piece) concentration. FIG. 4a-4c showed the counts of 3-5 subordinate microvessels in the area within 2.5 mm around the filter paper. FIG. 4a is the PBS group; FIG. 4b is the ZY3(10 μl/piece) group; FIG. 4c is the ZY3(50 μl/piece) group; FIG. 4d indicated that compared with the VEGF group, in the groups of VEGF+ small peptide ZY3 with different concentrations, the amount of neovascularization in chick embryo chorioallantoic membrane is significantly inhibited and the inhibition is concentration-dependent. **P<0.01. The differences are statistically significant.

Example 6

Detection of Inhibitation Effect of Small Peptide ZY3 on Pathological Angiogenesis in the Mouse Cornea Mice model of the corneal stroma micropocket was used and the methods were as follows:
Male C57BL/6 mice (4-5 week old) were intraperitoneally injected with 2% pentobarbital (about 0.1 ml/mouse) for anesthesia. 4% hydrochloric oxybuprocaine ophthalmic solution was locally administrated. Under the stereo microscope, OT syringe needle and 2 ml syringe needle were used to perform a blunt dissection between the layers of corneal stroma at 0.8-1 mm from corneoscleral limbus. A pouch of about 0.6×0.8 mm was formed. Sustained-release granules (mixture of 1:1 (v/v) of 12% PolyHAME: sucralfate) were implanted respectively into the micropocket, including negative control group (blank granule), positive control group (VEGF group: 320 ng/µl, 160 ng/granule), and treatment group (VEGF+small peptides ZY3 of low concentration (1 µg/granule), or high concentration (2 µg/granule)). 5 days after operation, the length of the longest new vessel (VL is the length of the longest new blood vessel grown from limbus to the cornea), and the clock hours of corneal neovascularization (CN represents the accumulative clock hours of corneal neovascularization) were observed. Neovascularization area were calculated as followed: Area (mm$^2$)=0.5*3.14*VL (mm)*CN*0.4 (mm) SPSS1L 0.1 was used for statistical analysis.

Figure 5:
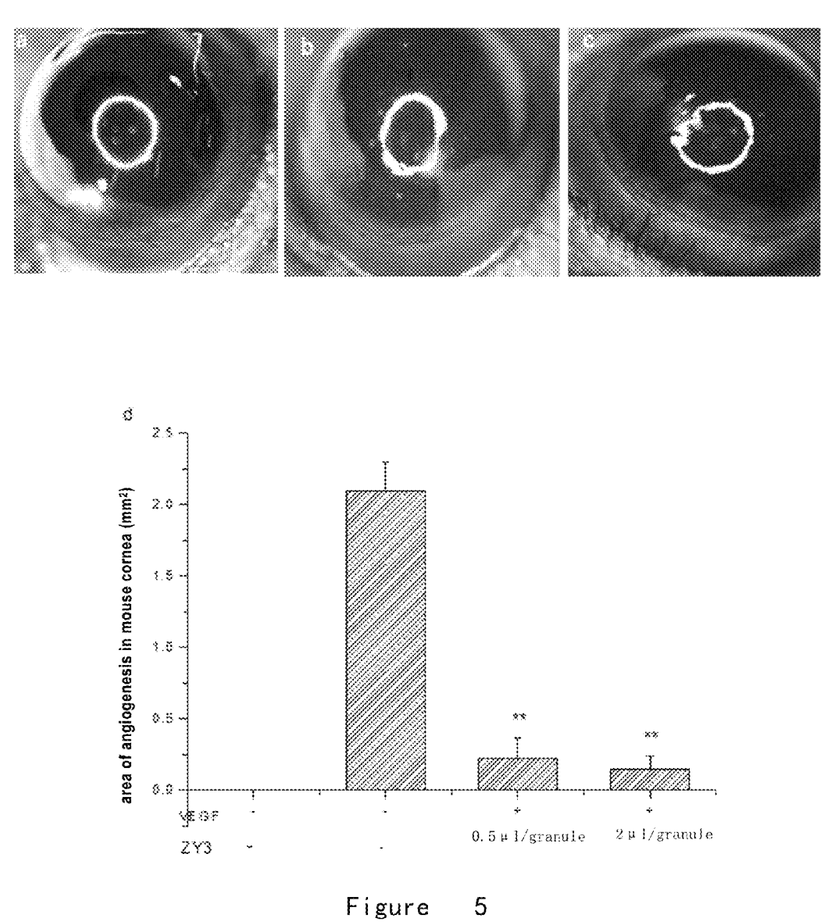
FIG. 5 shows the effect of small peptide ZY3 on pathological angiogenesis in mouse cornea. Small peptide ZY3 exhibits a significant inhibition effect on angiogenesis.

The results shown in FIG. 5 indicated that compared with the VEGF group, Small peptide ZY significantly inhibited the corneal angiogenesis both in low concentration (0.5 µg/granule) and high concentration (2 mg/granule) (see the note). FIG. 5 showed the effect of small peptide ZY3 on pathological angiogenesis in mouse cornea, which demonstrated that small peptide ZY3 significantly inhibits angiogenesis. FIG. 5a-5c show the neovascularization area on mouse cornea. FIG. 5a is the VEGF group; FIG. 5b is the ZY3(0.5 µl/granule) group; FIG. 5c is the ZY3(2 µl 1/granule) group; FIG. 5d indicated that compared with the VEGF group, in the groups of VEGF+small peptide ZY3 with different concentrations, the pathological angiogenesis in mouse cornea was significantly inhibited. **P<0.01. The differences are statistically significant.

Example 7

Preparation of Eyedrop

The following components were mixed via the conventional techniques to obtain a 1% eyedrop, the formulation of which was listed as follows:

| | |
|---|---|
| ZY3 peptide (ZY3) | 10 mg |
| Hydroxylpropyl methyl celloluse | 0.03 g |
| Sterile water | q.s. to 10 ml |

The osmotic pressure was adjusted to 300 Osm, and the pH was adjusted to 6.8-7.1.

Five volunteers used the eyedrop for one week, three times per day, and 1 drop/eye for each time. The results showed that the eyedrop could inhibit ocular angiogenesis.

Example 8

Preparation and Activity of Derived Polypeptides

Derived Polypeptides were prepared as follows, and the inhibition effect of each ZY3 derived polypeptides on proliferation of Human Umbilical Vein Endothelial Cells HUVECs was determined according to the methods in Example 3.

Derived Polypeptide 1: the sequence was the same as SEQ ID NO.: 1 except that Val at position 4 was substituted by Ile.

Derived Polypeptide 2: the sequence was the same as SEQ ID NO.: 1 except that Arg at position 12 was substituted by Pro.

Derived Polypeptide 3: the sequence was the same as SEQ ID NO.: 1 except that Asp at position 15 was substituted by Glu.

Derived Polypeptide 4: the sequence was the same as SEQ ID NO.: 1 except that Thr at position 23 was substituted by Arg.

Derived Polypeptide 5: the sequence was the same as SEQ ID NO.: 1 except that Leu at position 8 was deleted.

The results indicated that in the treatment group (1 µg/µl) of the above derived polypeptides 1-5, the proliferation of HUVEC was significantly inhibited.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

What we claimed are:

1. A pharmaceutical composition, comprising:
(a) a polypeptide consisting of the following formula I, or a pharmaceutically acceptable salt thereof,

[Xaa0]-[Xaa1]-[Xaa2]-[Xaa3]-[Xaa4]-[Xaa5]-[Xaa6]-

[Xaa7]-[Xaa8]-[Xaa9]-[Xaa10]-[Xaa11]-[Xaa12]-

[Xaa13]-[Xaa14]-[Xaa15]-[Xaa16]-[Xaa17]-[Xaa18]-

[Xaa19]-[Xaa20]-[Xaa21]-[Xaa22]-[Xaa23]-[Xaa24]-

[Xaa25]-[Xaa26]-[Xaa27]-[Xaa28]   (I)

wherein,
Xaa0 is selected from Lys, Glu, Pro-Ile-Lys, and Ile-Lys;
Xaa1 is selected from the group consisting of Thr and Ser;
Xaa2 is selected from the group consisting of Ala, Val, Leu and Ile;
Xaa3 is selected from the group consisting of Asn, Gln, His, Lys or Arg;
Xaa4 is selected from the group consisting of Val, Ile, Leu, Met, Phe and Ala;
Xaa5 is selected from the group consisting of Thr and Ser;
Xaa6 is selected from the group consisting of Met, Leu, Phe, and Ile;
Xaa7 is selected from the group consisting of Gln and Asn;
Xaa8 is selected from the group consisting of Leu, Ile, Val, Met, Ala and Phe;
Xaa9 is selected from the group consisting of Leu, Ile, Val, Met, Ala and Phe;
Xaa10 is selected from the group consisting of Lys, Arg, Gln and Asn;
Xaa11 is selected from the group consisting of Ile, Leu, Val, Met, Ala and Phe;
Xaa12 is selected from the group consisting of Arg, Pro, Lys, Gln and Asn;
Xaa13 is selected from the group consisting of Ser and Thr;
Xaa14 is selected from the group consisting of Gly, Pro, and Ala;
Xaa15 is selected from the group consisting of Asp, Glu;
Xaa16 is selected from the group consisting of Arg, Lys, Gln and Asn;
Xaa17 is selected from the group consisting of Pro and Ala;
Xaa18 is selected from the group consisting of Ser and Thr;
Xaa19 is selected from the group consisting of Tyr, Trp, Phe, Thr and Ser;
Xaa20 is selected from the group consisting of Val, Ile, Leu, Met, Phe and Ala;
Xaa21 is selected from the group consisting of Glu and Arg;
Xaa22 is selected from the group consisting of Leu and Ser;
Xaa23 is selected from the group consisting of Thr and Arg;
Xaa24 is selected from the group consisting of Phe and Ser;
Xaa25 is selected from the group consisting of Ser and Arg;
Xaa26 is selected from the group consisting of Gln and Ser;
Xaa27 is selected from the group consisting of His and Arg;
Xaa28 is absent, or a peptide segment consisting of 1-3 amino acids;
and said polypeptide exhibits an activity of inhibiting angiogenesis; and
(b) a pharmaceutically acceptable carrier or excipient,
wherein the polypeptide is present in an amount effective for treating a disease associated with angiogenesis, and wherein the amount is 10μ to 100 mg.

2. The pharmaceutical composition of claim 1, wherein Xaa28 is a peptide segment consisting of 3 amino acids.

3. The pharmaceutical composition of claim 1, wherein Xaa0 is Lys.

4. A pharmaceutical composition comprising a polypeptide or a pharmaceutically acceptable salt thereof, and a pharmaceutically acceptable carrier or excipient, wherein said polypeptide is selected from the group consisting of:
(a) a polypeptide consisting of SEQ ID NO:1;
(b) a polypeptide which is derived from the polypeptide of (a) by substitution or deletion of 1-2 amino acids in the amino acid sequence of SEQ ID NO: 1, or addition of 1-3 amino acids at the C-terminus and which has an activity of inhibiting angiogenesis;
wherein, the homology between the derived polypeptide and SEQ ID NO: 1 is ≥95%.

5. An isolated nucleic acid molecule encoding the polypeptide of claim 1.

6. The pharmaceutical composition of claim 1, wherein the dosage form of the composition is injection solution, eyedrop, ophthalmic gel or eye ointment.

7. A method for inhibiting angiogenesis in a mammal, comprising the step of administering a subject in need thereof with the polypeptide or a pharmaceutically acceptable salt thereof according to claim 1.

8. The method of claim 7, wherein, said angiogenesis is selected from the group consisting of neovascular eye diseases, tumor, ischemic heart disease, non-inflammatory myocardiopathy, coronary sclerosis, arteriosclerosis obliterans, artery embolism, artery thrombus, Berger's disease, chronic inflammation, inflammatory intestinal diseases, ulcer, rheumatic arthritis, scleroderma, psoriasis, infertility and sarcoma-like diseases.

9. The pharmaceutical composition of claim 4, wherein the dosage form of the composition is injection solution, eyedrop, ophthalmic gel or eye ointment.

10. A method for inhibiting angiogenesis in a mammal, comprising the step of administering a subject in need thereof with the polypeptide or a pharmaceutically acceptable salt thereof according to claim 4.

* * * * *

SEQUENCE LISTING

```
<160> NUMBER OF SEQ ID NOS: 2

<210> SEQ ID NO 1
<211> LENGTH: 27
<212> TYPE: PRT
<213> ORGANISM: Artificial Sequence
<220> FEATURE:
<223> OTHER INFORMATION: angiogenesis-inhibiting peptide ZY3

<400> SEQUENCE: 1

Thr Ala Asn Val Thr Met Gln Leu Leu Lys Ile Arg Ser Gly Asp Arg
1               5                   10                  15

Pro Ser Tyr Val Glu Leu Thr Phe Ser Gln His
            20                  25

<210> SEQ ID NO 2
<211> LENGTH: 81
<212> TYPE: DNA
<213> ORGANISM: Artificial Sequence
<220> FEATURE:
<223> OTHER INFORMATION: encoding sequence for angiogenesis-inhibiting
      peptide ZY3
```

```
<400> SEQUENCE: 2
acggccaatg tcaccatgca gctcctaaag atccgttctg gggaccggcc ctcctacgtg        60
gagctgacgt tctctcagca c                                                  81
```